US005549577A

United States Patent [19]

Siegel et al.

[11] Patent Number: 5,549,577
[45] Date of Patent: Aug. 27, 1996

[54] NEEDLELESS CONNECTOR

[75] Inventors: Geoffrey S. Siegel; Karl R. Leinsing, both of Raleigh, N.C.

[73] Assignee: Ivac Corporation, San Diego, Calif.

[21] Appl. No.: 174,843

[22] Filed: Dec. 29, 1993

[51] Int. Cl.⁶ .......................... A61M 5/00; A61M 25/00; F16K 51/00
[52] U.S. Cl. ...................... 604/256; 604/283; 251/149.1
[58] Field of Search .................... 604/86, 89–91, 604/244, 246, 247, 249, 256, 264, 283, 905, 167; 251/149, 149.1, 341, 342, 347–349, 354

[56]  References Cited

U.S. PATENT DOCUMENTS

| | | |
|---|---|---|
| 811,811 | 2/1906 | Allison . |
| 1,180,665 | 4/1916 | McElroy . |
| 2,579,724 | 12/1951 | Breakstone . |
| 2,999,499 | 9/1961 | Willet . |
| 3,570,484 | 3/1971 | Steer . |
| 3,837,381 | 9/1974 | Arroyo . |
| 3,994,293 | 11/1976 | Ferro . |
| 4,000,739 | 1/1977 | Stevens . |
| 4,063,555 | 12/1977 | Ulinder . |
| 4,080,965 | 3/1978 | Phillips . |
| 4,197,848 | 4/1980 | Garrett et al. . |
| 4,240,411 | 12/1980 | Hosono . |
| 4,324,239 | 4/1982 | Gordon et al. . |
| 4,334,551 | 6/1982 | Pfister . |
| 4,421,123 | 12/1983 | Percarpio . |
| 4,449,693 | 5/1984 | Gereg . |
| 4,475,548 | 10/1984 | Muto . |
| 4,496,348 | 1/1985 | Genese et al. . |
| 4,512,766 | 4/1985 | Vailancourt ............................ 604/169 |
| 4,655,752 | 4/1987 | Honkanen et al. . |
| 4,745,950 | 5/1988 | Mathieu . |
| 4,752,287 | 6/1988 | Kurtz et al. . |
| 4,809,679 | 3/1989 | Shimonaka et al. . |
| 4,863,201 | 9/1989 | Carstens . |
| 4,908,018 | 3/1990 | Thomsen . |
| 4,915,687 | 4/1990 | Sivert . |
| 5,006,118 | 4/1991 | Yule . |
| 5,041,087 | 8/1991 | Loo et al. . |
| 5,049,128 | 9/1991 | Duquette . |
| 5,061,253 | 10/1991 | Yoshida . |
| 5,064,416 | 11/1991 | Newgard et al. ....................... 604/167 |
| 5,071,404 | 12/1991 | Larkin et al. . |
| 5,078,699 | 1/1992 | Harber et al. . |
| 5,080,654 | 1/1992 | Picha et al. . |
| 5,100,394 | 3/1992 | Dudar et al. . |
| 5,108,380 | 4/1992 | Herlitze et al. . |
| 5,122,123 | 6/1992 | Vaillancourt ............................ 604/192 |
| 5,127,904 | 7/1992 | Loo et al. . |
| 5,135,489 | 8/1992 | Jepson et al. . |
| 5,147,333 | 9/1992 | Raines . |
| 5,154,703 | 10/1992 | Bonaldo ................................. 604/244 |
| 5,158,554 | 10/1992 | Jepson et al. . |

(List continued on next page.)

FOREIGN PATENT DOCUMENTS

| | | |
|---|---|---|
| 2083670 | 5/1993 | Canada . |
| 1634936 | 3/1991 | U.S.S.R. ............................ 251/149.1 |
| WO93/11828 | 6/1993 | WIPO . |

*Primary Examiner*—John D. Yasko
*Assistant Examiner*—Adam J. Cermak
*Attorney, Agent, or Firm*—Fulwider Patton Lee & Utecht

[57]  ABSTRACT

A needleless connector allowing infusion and withdrawal of fluid in medical applications is disclosed. The injection site has a housing which contains a blunt cannula within it. An elastomeric pre-slit plunger is movably carried within the housing by the housing and said blunt cannula. Insertion of a connector moves the elastomeric pre-slit plunger from a first, occluding position deeper into the housing and over the blunt cannula to a second position, where the pre-slit portion of the plunger is penetrated by the blunt cannula. This opens a fluid passage from the inserted connector through the cannula to the opposite end of the housing, allowing fluid flow through the connector. Pressurized gas within the housing, or an elastically deformable member, or the two in combination, bias the elastomeric plunger back to its first position. As an inserted connector is removed, the fluid pathway through the injection site is re-sealed.

24 Claims, 2 Drawing Sheets

U.S. PATENT DOCUMENTS

| | | |
|---|---|---|
| 5,163,922 | 11/1992 | McElveen, Jr. et al. . |
| 5,167,648 | 12/1992 | Jepson et al. . |
| 5,171,234 | 12/1992 | Jepson et al. . |
| 5,184,652 | 2/1993 | Fan . |
| 5,188,620 | 2/1993 | Jepson et al. . |
| 5,190,067 | 3/1993 | Paradis et al. . |
| 5,199,948 | 4/1993 | McPhee . |
| 5,203,775 | 4/1993 | Frank et al. . |
| 5,211,638 | 5/1993 | Dudar et al. . |
| 5,215,537 | 6/1993 | Lynn et al. . |
| 5,215,538 | 6/1993 | Larkin . |
| 5,230,706 | 7/1993 | Duquette . |
| 5,234,410 | 8/1993 | Graham et al. ............ 604/167 |
| 5,242,393 | 9/1993 | Brimball et al. . |
| 5,269,771 | 12/1993 | Thomas et al. ............ 604/213 |
| 5,273,533 | 12/1993 | Bonaldo ..................... 604/83 |
| 5,279,571 | 1/1994 | Larkin . |
| 5,280,876 | 1/1994 | Atkins ..................... 251/149.1 |
| 5,330,435 | 7/1994 | Vaillancourt ............ 604/167 |
| 5,360,413 | 11/1994 | Leason et al. ............ 604/249 |

5,549,577

NEEDLELESS CONNECTOR

BACKGROUND OF THE INVENTION

This invention generally relates to connectors of the type used in the handling and administration of parenteral fluids and, more particularly, to a connector adapted to make sterile connections in medical systems without the use of a sharp cannula.

Injection sites for injecting or removing fluid from a system, such as an IV infusion set connected to a patient, or a fluid reservoir or drug vial, are wellknown and widely used. Conventional injection sites generally involve a pierceable septum formed of an elastomeric material such as latex rubber or the like, captured in an access port. The housing of the septum may be, for example, the Y-body of a conventional Y-site component of an IV delivery set. A sharp cannula is inserted into the access port, piercing the septum, and a distal end of the cannula is positioned distal of the septum. In this way a fluid connection is made with the Anterior of the access port through the inserted cannula. Upon withdrawal of the sharp cannula, the elastomeric septum reseals the puncture made by the now-withdrawn cannula. Thus a sterile environment can be maintained within the housing of the injection site. The outer surface of the septum of the injection site is wiped with an antiseptic before each use to prevent septic agents from being drawn into the access port by the piercing movement of the needle.

Recently, connectors for accommodating injection and withdrawal of fluids without the use of sharp cannulas have been used in increasing numbers instead of conventional injection sites. This is, at least in part, due to concern regarding the transmission of blood-borne diseases through accidental needle punctures of the person handling the sharp cannula. Connectors having no sharpened surfaces are desirable because the chances of inadvertently piercing the operator's skin are lessened.

However, some existing needleless connectors allow fluid flow in only one direction, or require some further manipulation after a connection is established to allow fluid flow in both directions. Both of these characteristics are undesirable because they limit the usefulness of the connector. A further concern in the design of needleless connectors is the order of occurrences in which the connection is made. For example, allowing fluid to escape or air to enter during connection due to the female connector being opened before the male connector is sufficiently seated are undesirable.

Additionally, some existing connectors accommodate a relatively large interior fluid volume, requiring injection of a commensurately large volume of fluid just to fill the connector. If not taken into account, this fluid volume can detract from the volume of medicament injected and may be clinically significant. An inconvenient separate flushing procedure may be required in low dose injections or in the injection of unstable medicines due to this relatively large interior volume.

Moreover, relatively complex geometries and provision of springs and the like in the wetted portion of the connector interior may give rise to "dead spaces", where fluid tends to linger due to poor flushing. Dead spaces give rise to problems similar to those occasioned by large interior volumes, again resulting in the inconvenient requirement of flushing.

A further concern regarding the design of a needleless connector is that it should not accommodate a conventional sharp needle. Where such connectors can be used with sharp and blunt cannulas, the deterrent effect with regard to using sharp needles to make fluid connections, with an associated reduction in the number of accidental needle sticks, is potentially compromised.

Furthermore, it is desirable that needleless connectors be configured so that they can be easily cleaned by an antiseptic wipe or otherwise sterilized prior to making a connection. All exterior surfaces that may be involved in the transmission of fluid should be available for cleaning prior to the connection being made. Some prior connectors have a small rift or fissure, defined by a clearance between parts or an elastomeric element that is not under sufficient compression, at the proximal or connecting end. Such a feature is difficult and inconvenient to clean in attempting to sterilize a connector. Alternatively, connectors requiring a cap to maintain a sterile connection port are undesirable because the extra steps of removing and replacing a cap are inconvenient for medical personnel.

Another important characteristic of a needleless connector is its ability to hold a vacuum from a distal side. That is to say, if a vacuum is applied to the interior of the connector, the connector should not admit air. This becomes an increased concern in connectors that have been used at least once. Adverse consequences may result if a connector cannot hold a vacuum, for example, some automated infusion pumps wall pull a vacuum in a tubing line under certain circumstances. Needlelees connectors that will not hold a vacuum, incorporated in an infusion get used with such a pump, may admit air when no connector or cap is attached, which may in turn cause a potentially harmful air embolism in a patient.

The ability to accommodate a high fluid flow rate is also desirable in a needleless connector. Physicians in certain situations order the administration of medicaments at high flow rates. Some prior connectors have restrictive geometries, which limit their flow capacity such that administering fluids at high rates is inconvenient for medical personnel. Often flow rate requirements cannot be met under gravity head flow conditions.

Lastly, some existing needleless connectors have a relatively complex configuration and large number of parts. Such connectors are difficult and costly to manufacture, and may have more problems in service, such as sticking due to the difficulty flushing medicaments from small dead spaces inherent in complex geometries referred to above.

Consequently, there is a continuing need, for a variety of reasons, for improvements in injection sites. The present invention fulfills this need.

SUMMARY OF THE INVENTION

Briefly, and in general terms, the invention provides a needleless connector of relatively simple design and few parts which is intuitive to use and which is relatively inexpensive to manufacture, accommodates a high flow rate, is more easily cleaned before use, and does not require a protective cap. The design minimizes unwanted fluid and air leakage, has minimal interior fluid volume and "dead space," and is not compatible with a sharp needle, thereby reducing accidental needle punctures of medical personnel.

More specifically, the connector of the invention includes a housing having first and second ends, defining a chamber therebetween, the first end defining a connection port. A blunt cannula is carried by the housing within the chamber, the blunt cannula having a fluid passage therethrough in fluid communication with the second end of the housing. An elastomeric pro-slit plunger is movably disposed in the housing in a first position within the connector. In this first position the elastomeric pro-slit plunger sealingly occludes the passage through the cannula at the proximal end of the cannula. When moved to a second position within the chamber the elastomeric pro-slit plunger is penetrated by said blunt cannula so that the first and second ends of the housing are in fluid communication by means of the passage through said blunt cannula.

In a more detailed aspect, a biasing means is included for biasing the plunger to the first position within the chamber. This biasing means is, for example, either a deformable spring-like or other elastic member, a pressurized gas within the chamber, or a combination of both.

In another detailed aspect, when the elastomeric plunger is in the first position, it is flush with the first end of the connector. The elastomeric plunger is in radial compression in this area, eliminating any annular crack or fissure that might otherwise exist between the plunger and the housing, and the slit portion is held tightly shut. As a result, there is no place for pooling of fluid or other contaminants in the outer geometry, and the connector can be easily cleaned, for example with an alcohol swipe, to sterilize it before connection. These features eliminate the need for a separate cap, and make the connector according to the invention convenient for medical personnel to use, with attendant time and cost savings. Moreover, the design reduces the chance of an infection being transmitted through the connector, and the configuration also allows the connector to hold a vacuum within the chamber without admitting outside air.

In further detailed aspects of the invention, a significant portion of the fluid pathway between the first and second ends of the connector 10, in making a fluid connection, comprises the blunt cannula 30, which has a small fluid volume associated with it. Consequently, the connector as a whole defines a flow channel therethrough that has a relatively small interior fluid volume, reducing the need for flushing. At the same time, the connector can accommodate a relatively high fluid flow rate, as the flow channel is straight and is not restricted. Dead space associated with the connector is commensurately small.

Lastly, to reduce the number of component parts, the blunt cannula can be formed unitary with the housing member. This results in three component parts being required if a two-piece housing is used.

The connector of the invention, with its simple construction and small number of parts provides manufacturing cost savings, as well as enhancing safety, reliability and ease of use in preparing medications and treating patients. These and other features and advantages of the invention will become more apparent from the following detailed description, taken in conjunction with the accompanying exemplary drawings.

DETAILED DESCRIPTION OF THE PREFERRED EMBODIMENTS

Figure 1:
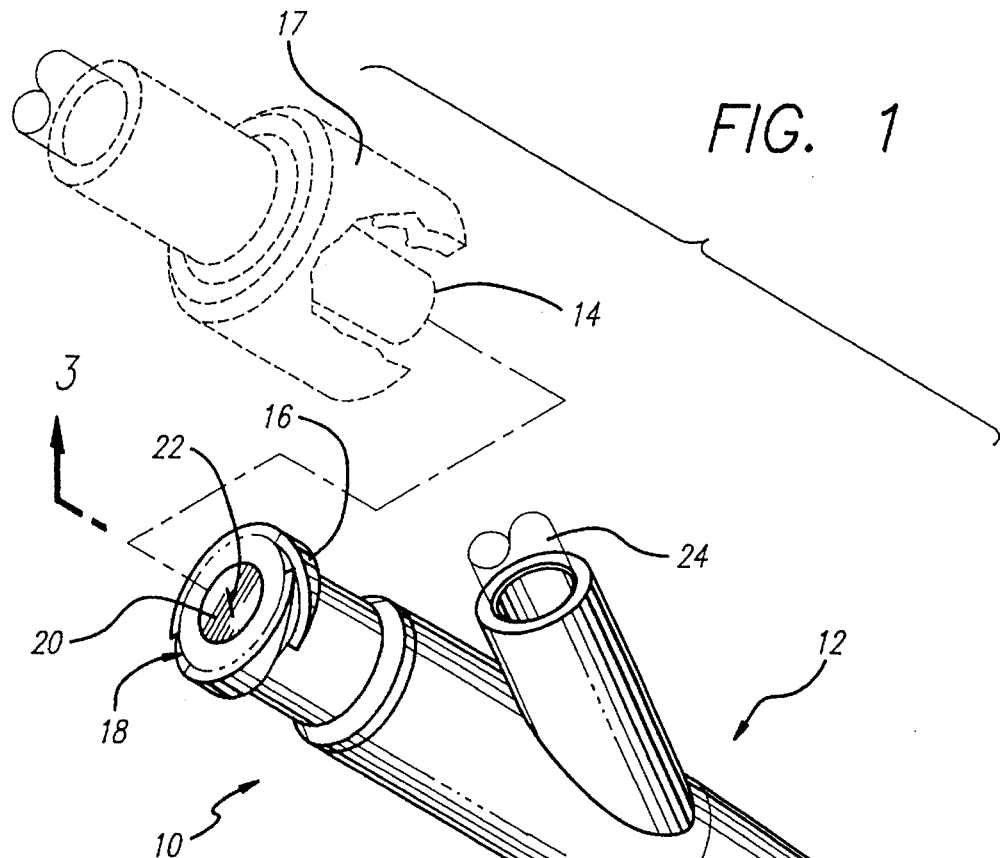
FIG. 1 is a perspective view of a connector embodying features of the invention.

As shown in FIG. 1 for purposes of illustration, the invention is embodied in a self-sealing fluid connector of the type generally known in the art as a "needleless" connector 10, more specifically in the body of a Y-site 12. The connector is capable of receiving a compatible connector incorporating a blunt cannula, such as a male luer connector fitting 14 (with or without a luer look 16, 17) in a female luer connection port 18, displacing an elastomeric plunger 20.

When no male connector 14 is inserted, the elastomeric plunger 20 is at a first position at a proximal end of the connector, flush with the connection port 18. The well of the female connection port is completely sealed by the elastomeric plunger, and there is no opportunity for fluid to pool in the exterior geometry of the connector. This configuration also allows the connector to be easily wiped, for example by an alcohol swipe (not shown). These features reduce the chance that infectious agents will be introduced into the interior of the connector when a male connector is inserted.

The elastomeric plunger 20 is pre-slit by a single longitudinal slit 22. The slit is closed when no connector 14 is inserted into the connector 10. The elastomeric plunger is radially sized slightly larger than the connection poet 18 at its proximal end, and as a consequence, is under radial compression as it rests within the female luer connection port. The plunger can be eccentric in cross-section in this regard, the dimension where the plunger is thickest coinciding with the direction of application of pressure calculated to most effectively close the slit 22. This holds the walls of the pro-slit portion tightly together so that a seal against passage of liquids, gasses and pathogens will be formed by the elastomeric plunger in the luer connection port 18. Also, compression of the plunger at its proximal end eliminates the annular crack or fissure between the plunger and the walls of the connection port that otherwise might allow pooling of liquids or harbor pathogens. These features, combined with the proximal end of the elastomeric plunger being flush with the connector port 18 for easy sterilization, make it unnecessary to use a separate cap (not shown) to protect the connector from contamination.

In use, the connector 10 incorporated in a Y-site 12 is typically connected to flexible tubing fluid lines 24, 26 of a fluid system, Such a system might be for example an IV administration set (not shown), connected through a venipuncture site to the circulatory system of a patient.

Figure 2:
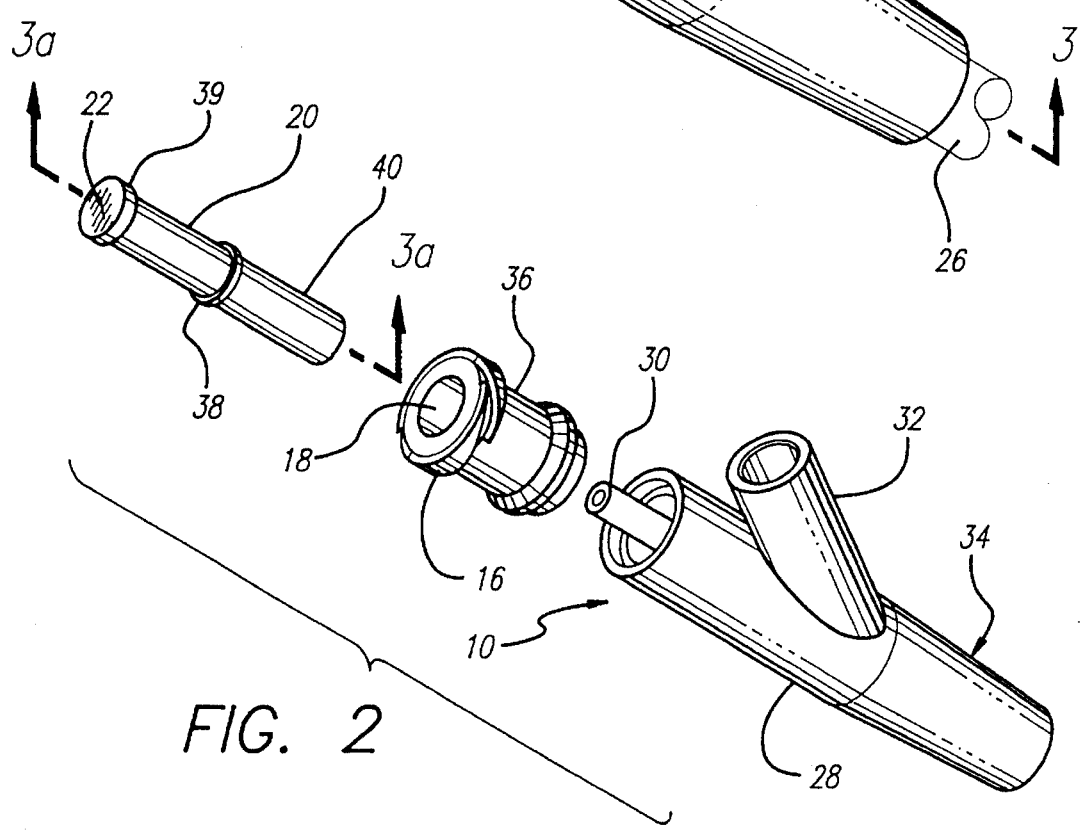
FIG. 2 is an exploded perspective view of the connector shown in FIG. 1.

Turning to FIG. 2, in the illustrated embodiment the needleless connector 10 is formed of three parts. The simplicity of design and small number of parts are highly advantageous in terms of reliability, ease of manufacture and use, and cost. A distal housing member 28 is formed of a resilient plastic material in this embodiment and incorporates a blunt cannula 30 which is preferably formed of the same material as the housing member 28, and is of unitary construction therewith. Alternatively, the blunt cannula could be a separate member formed of a different material, integrated into the housing member. The housing member also incorporates tubing connector portions 32, 34 for connecting to flexible tubing lines 24, 26 (FIG. 1).

A proximal connection port housing member 36 is joined to the distal housing member 28 to form the housing of the needleless connector 10. The connection port housing member 36 incorporates the female luer connection port 18 and luer lock 16 of the connector. The connection port housing member is preferably made of the same material as the distal housing member, and the two housing members are Joined by conventional methods of bonding such as ultrasonic or solvent welding, for example. As will be apparent to one skilled in the art, the two housing potions could also be made of differing materials.

After the two housing members 28, 36 are joined, the elastomeric plunger 20 is inserted through the luer connector port 18 into the joined housing members 28, 36. A Food and Drug Administration (FDA) approved silicone lubricant may be used to facilitate this process, as well as to aid in operation of the connector as discussed below. The insertion of the elastomeric plunger causes gas (such as air or another selected gas) inside the joined housing members to be pressurized. Pressure within the housing can be controlled by adjusting the speed of insertion of the plunger, and/or partially or completely occluding the tubing connectors 32, 34 whale the plunger is being inserted. After insertion of the plunger an annular stop ring 38 interacts with the proximal connection port housing member 36 to retain the plunger in the housing, and thereby maintain the pressurized state of the gas within the housing.

The elastomeric plunger 20 in the illustrated embodiment also has a proximal seal portion 39 which provides a seal against contaminants, and radial compression of the plunger where it incorporates the slit 22 at the proximal end as discussed above. The plunger also includes a cylindrical sleeve portion 40. The plunger is preferably formed of a self-lubricating silicone rubber in this embodiment which is impregnated with an FDA approved silicone lubricant. Alternatively, an elastomeric material having similar properties could be used, in combination with an FDA approved silicone lubricant conventionally applied. During assembly, the cylindrical sleeve portion is guided into correct position by the blunt cannula member 30 which it fits over.

Figure 3:
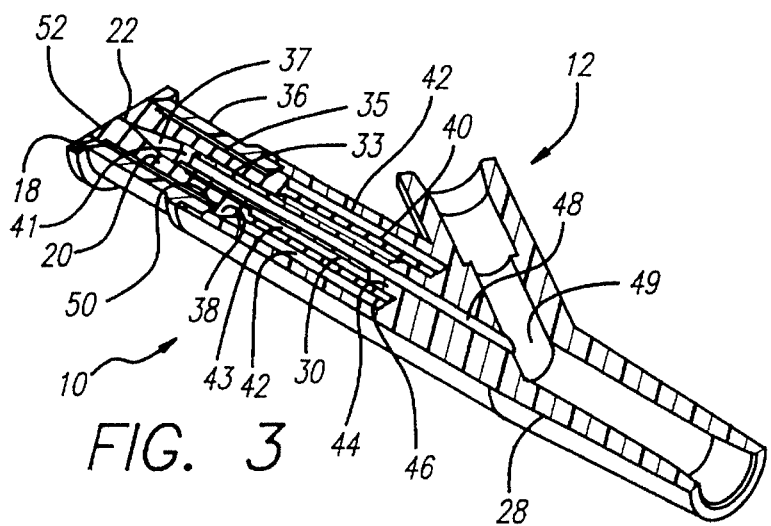
FIG. 3 is a longitudinal cross-sectional view of a needleless connector in accordance with the invention, taken along line 3—3 in FIG. 1.
Figure 3A:
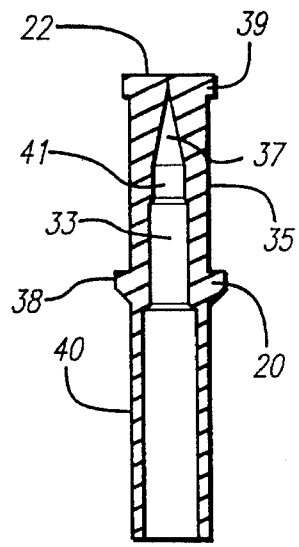
FIG. 3a is a longitudinal cross-sectional view of component of a connector of the invention, taken along line 3a—3a in FIG. 2.

Turning to FIG. 3, the interaction of the various members 20, 28, 36 in the assembled connector 10 can be seen more clearly. The plunger 20 is at a first position within the assembled housing 28, 36 wherein the connector is closed and sealed. A cylindrical blunt cannula receiving portion 41 is formed in the interior of the plunger, and is sealingly disposed about the first or proximal end of the blunt cannula 30. The cylindrical blunt cannula receiving portion and the pro-slit portion 22 of the plunger are connected by a transition portion 37. The blunt cannula receiving portion can be configured to have different diameter segments along its longitudinal dimension. For example, a distal relieved portion 33 which is not compressed against the blunt cannula when the plunger is in its first position has a larger diameter than the rest of the blunt cannula receiving portion 41. This is more clearly shown in FIG. 3a. The relieved portion allows easier movement of the plunger over the blunt cannula.

The elastomeric plunger 20 also incorporates a relived portion 35 on its outer circumferential surface between the annular stop ring portion 38 and the proximal seal portion 39. This portion is under less radial compression than that at the location of the slit 22 and the proximal seal portion. Silicone lubricant, if applied to the outer surface of the plunger, may be retained between the proximal seal portion and the annular stop ring 38 in the assembled connector 10. Due to these considerations, friction is reduced and movement of the plunger within the connector is improved.

Returning to FIG. 3, an outer sealed chamber 42 is formed within the distal housing member 28 between the cylindrical sleeve portion 40 of the elastomeric plunger 20 and the housing walls. An inner sealed chamber 43 is formed between the cylindrical sleeve portion and the blunt cannula member 30. As mentioned, gas within these chambers may be pressurized upon assembly of the connector.

The blunt cannula 30 in the illustrated embodiment has a cylindrical base portion 44 which carries a distal end 46 of the cylindrical sleeve portion of the elastomeric plunger 20. The interior of the blunt cannula is in fluid communication with, and forms an extension of, a fluid conduit 48. The fluid conduit 48 may be placed in fluid communication with an external fluid delivery system, such as an IV administration set connected to, a venipuncture site in a patient (not shown) byway of a passageway 49 through the Y-site 12. The fluid conduit 48 and cannula 30 form a fluid pathway which is closed at its proximal end by the plunger 20 when the plunger is at a first position at the proximal end of the connector 10.

The elastomeric plunger 20 is partially penetrated in this embodiment by the blunt cannula member 30 through the blunt cannula receiving portion 41 when the elastomeric plunger is in the first position as discussed above, and the plunger is biased to this position by a force caused by pressurized gas in the sealed chambers 42 and 43. The plunger is also biased to the first position by a force produced by the cylindrical sleeve portion 40 of the elastomeric plunger seeking its un-deformed shape. In an alternate embodiment, a spring or the like could be substituted for the cylindrical sleeve portion to produce a biasing force in a similar manner. These forces push the plunger against the connection port housing member 36. The distal end of the connection port housing member 36 forms an annular ledge 50, on which the annular stop ring portion 38 of the elastomeric plunger 20 catches, to retain the plunger in the connector 10.

The configuration of the connector 10 when the elastomeric plunger 20 is in the first, or sealed, position allows it to maintain a seal against both positive and negative pressures. If a vacuum is drawn within the connector, the sides of the transition portion 37 and, consequently, the pro-slit portion 22 are drawn more tightly together to form a tighter seal. This is advantageous in applications where a vacuum may be present in a connected fluid line, for example in and IV system (not shown) that includes an automated infusion pumping device, so that no air is drawn into the IV system through the connector 10.

Figure 4:
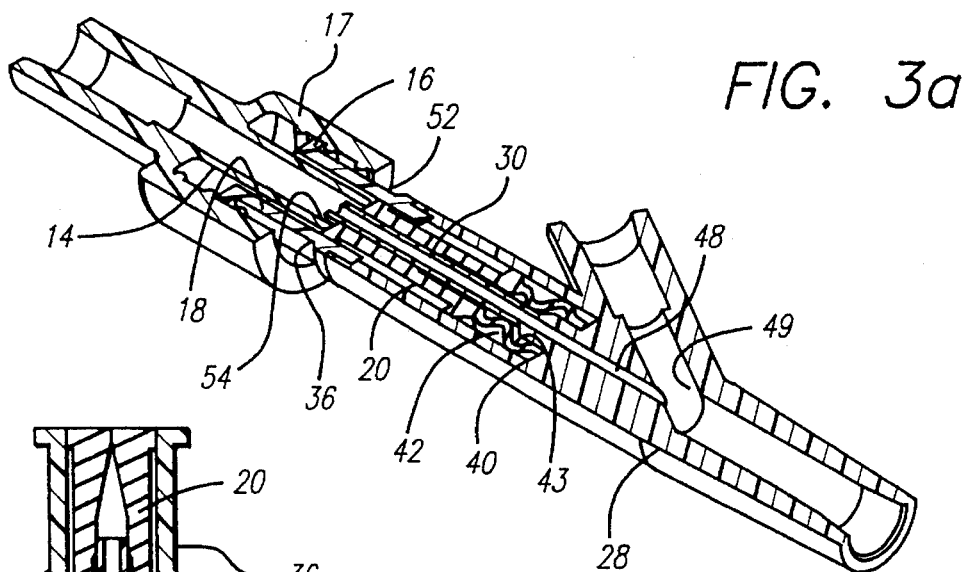
FIG. 4 is a longitudinal cross-sectional view of a connector according to the invention as shown in FIG. 3, showing a male fitting connected.

Referring to FIG. 4, when a male luer fitting 14 is inserted into the female luer connection port 18, the male luer fitting first contacts the proximal end surface 52 of the elastomeric plunger 20, forming a fluid-tight seal as the male luer fitting is advanced into the female connector port 18 against the biasing force described herein. This acts to eliminate fluid leaks from the needleless connector 10 during connection of a male luer fitting, and helps prevent the introduction of pathogens into the connector.

Insertion of the male luer fitting 14 moves the elastomeric plunger 20 dietally to a second position, and further pressurizes gas within the sealed chambers 42, 43. Insertion also causes elastic deformation of the cylindrical sleeve portion 40 of the elastomeric plunger, giving rime to a restoring force. The biasing force on the plunger caused by these two consequences of connection urge the plunger tightly against the inserted male luer fitting.

As can be appreciated with reference to the illustrated embodiment, when the male luer fitting 14 is fully inserted and the elastomeric plunger 20 is moved to its second position the proximal surface 52 of the plunger is positioned distally of the proximal end 54 of the blunt cannula 30. The blunt cannula extends into the inserted male luer fitting 14. To open the connector 10 for injection or withdrawal of fluid through it, the proximalend 52 of the plunger need only be pressed to a position distal to the proximal end of the blunt cannula so that the pre-slit portion 22 of the plunger does not cover the cannula 30 opening. It is apparent from FIG. 4 that the connector will accommodate a range of male luer fitting sizes and yet allow proper positioning of the proximal end of the plunger in operation. The configuration allows considerable leeway in this regard. However the biasing force will be greater with deeper penetration of the luer fitting, due to greater deformation of the elastomeric sleeve 40, and greater compression of the gas in chambers 42 and 43.

The male luer fitting 14 is held in the female luer connection port 18 of the connector 10 by friction fit, or by means of luer lock fittings 16 and 17. With a male luer fitting 14 inserted, a fluid pathway is opened from the male luer fitting through the interior of the blunt cannula 30 and fluid conduit 48 to a passageway 49 in fluid communication with a system (not shown).

As will be apparent, the connector 10 has a very small interior fluid volume. The conduit 48, and its extension through the blunt cannula 30, are of relatively small cross-sectional area and length. Furthermore, dead space is minimized because the plunger 20 is sealingly pressed against the tip of an inserted male luer fitting 14 and only moves inwardly as far as the male connector is inserted. For example, in FIG. 4, the only dead space is the volume between the outer diameter of the blunt cannula and the inner diameter of the inserted male luer fitting in the small distance the male luer fitting 14 extends beyond the opening of the blunt cannula 30. Moreover, there are no springs, complex conduit arrangements, or the lake, in the flow stream. A spring used in place of the elastomeric sleeve portion 40 would also be disposed outside of the blunt cannula and therefore outside of the wetted portions of the connector. Consequently, the fluid pathway through the connector is small in terms of fluid volume, but is straight and unobstructed. The connector as a result is easier to prime, and is advantageous in administration of low volumes of medications, due to the small fluid volume required to fill the connector and the inherent flushing action resulting from the design. Nevertheless, it has been found that the connector accommodates a relatively high flow rate, in both gravity and pumped flow applications.

During withdrawal of the male luer fitting 14, the elastomeric plunger 20 moves distally toward its first position, and its proximal surface 52 stays in sealing contact with the male luer fitting being withdrawn, due to the biasing forces acting on the plunger. As mentioned the biasing forces are the result of compressed gas within the chambers 42 and 43 and the elastomeric sleeve 40 seeking its un-deformed shape. Lubricant facilitates movement of the plunger.

Thus a fluid seal is maintained between the male luer and the plunger until the plunger has returned to its first position, and the fluid pathway through the connector then closed. As with connection, this sealing action minimizes fluid leakage during disconnection and helps maintain an a-septic condition within the connector.

As can be appreciated with reference to FIGS. 3 and 4, another feature of the connector 10 is that while it allows a large blunt cannula such as a male luer fitting 14 to be connected, it will not accept a sharp needle (not shown). Due to the placement of the proximal end 54 of the blunt cannula 30 in the female connection port 18, a needle inserted into the elastomeric plunger 20 when it is in the first position as shown in FIG. 3 will likely catch on the blunt cannula, discouraging the attempt to insert a needle. Should a needle get past the blunt cannula 30, any attempt to inject or withdraw fluid wall be frustrated, as the needle would then be in one of the closed chambers 42 or 43 within the connector. Incompatibility with sharp needles reduces the likelihood of their attempted use with the connector, and reduces commensurately the risk of accidental needle punctures of users.

Figure 5:
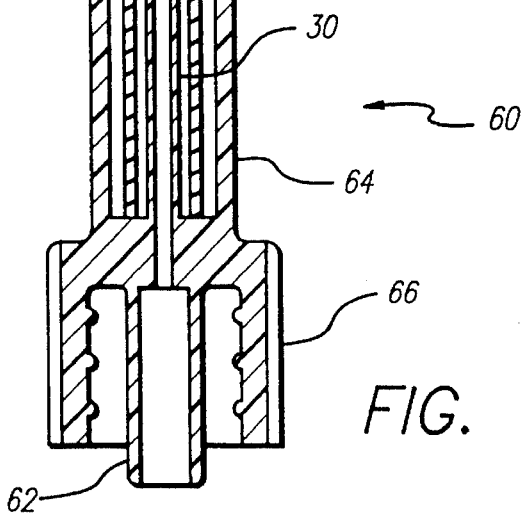
FIG. 5 is a longitudinal cross-sectional view of a second embodiment of the connector of the invention.

The needleless connector 10 of the invention has been shown embodied in a Y-site 12 in FIGS. 1–4, but the connector may be incorporated in other kinds of medical fluid handling and delivery apparatus. As an example, an alternate embodiment is shown in FIG. 5, where the needleless connector is incorporated in an adapter fitting 60 which can be attached to a standard female luer fitting (not shown) to provide a self-sealing needleless connector. The operation of the needleless connector is the same in this embodiment as that previously described. However, instead of a fluid pathway through the blunt cannula 30 and fluid conduit 48 opening into a Y-Site, the fluid conduit is in fluid communication with a standard male luer connector 62. A distal housing member 64 incorporates a luer lock 66.

From the above, it is evident that the present invention provides an advantageous needleless connector 10 constructed of relatively few parts, which is simple and reliable in operation, and can be manufactured at a relatively low cost. At the same time, the connector according to the invention allows safer and more convenient needleless handing and infusion of IV fluids in preparing medications and the treatment of patients. It is simple and intuitive to use, and further, provides advantages in sealing characteristics, low dead space and fluid volume, and improved flushing characteristics.

While several particular forms of the invention have been illustrated and described, it also will be appreciated that various modifications can be made to the present invention without departing from the spirit and scope thereof.

What is claimed:

1. A needleless connector for medical use, adapted to facilitate infusion and withdrawal of fluid therethrough, comprising:

a housing having a first end and a second end and a chamber therebetween, said first end defining a connection port;

a blunt cannula carded by the housing within the chamber, said blunt cannula having a proximal end and a distal end and a fluid passage therethrough in fluid communication with the second end of said housing;

an elastomeric pre-slit plunger slidably received within said housing and about said blunt cannula within the chamber, said plunger being configured so as to be oversized relative said housing and therefore under radial compression by said housing, and wherein said plunger slidable between a first position and a second position therein, which in the first position sealingly occludes the passage through the cannula at the proximal end thereof, and in a second position within said chamber is disposed distally over said blunt cannula so that the proximal end is not occluded and the first and second ends of said housing are in fluid communication by means of the passage through said cannula; and biasing means for biasing said elastomeric plunger to said first position, whereby insertion of a connector in said connection port moves said elastomeric plunger from said first position to said second position, and removal of said connector causes the elastomeric plunger to return to said first position.

2. The needless connector of claim 1, wherein the biasing means comprises a compressed gas disposed within the chamber of said housing.

3. The needleless connector of claim 1, wherein the biasing means comprises a collapsible elastomeric sleeve portion of said elastomeric plunger integral with said elastomeric plunger and carried by said housing.

4. The needleless connector of claim 1, wherein said blunt cannula is unitary with said housing.

5. The needleless connector of claim 1, wherein said connector port comprises a female luer adapter.

6. The needleless connector of claim 1, further comprising an inlet connector member having a proximal end and a distal end, and embodying said connection port, carried by said housing and comprising a proximal portion thereof, the distal end of said inlet connector member embodying an annular ridge for retaining said elastomeric plunger when assembled with said housing.

7. The needleless connector of claim 1, further comprising a lubricant applied to the elastomeric plunger whereby movement of said elastomeric plunger within said housing is facilitated.

8. A self-sealing connector adapted for making needleless fluid connections in medical fluid handling and administration applications, having a normally closed fluid flowpath therethrough which is opened by insertion of a compatible connector and closed by withdrawal of said compatible connector, comprising;

a housing, defining an interior chamber portion therein, a connector port portion having a proximal end, and a fluid conduit portion;

a blunt cannula, carded by said housing within the chamber portion, having a first end adjacent the connector port portion of said housing, and a second end in fluid communication with said fluid conduit portion, and having a fluid flowpath therethrough which extends from said first end of said blunt cannula to the fluid conduit portion of said housing;

an elastomeric plunger, having a pre-slit portion therethrough, adapted to receive said blunt cannula, slidably carded by the connector port portion of said housing and the blunt cannula, configured so as to be radially compressed by said connector port portion and slidable between a first position within the connector port portion wherein the plunger is flush with the proximal end, the slit portion is closed to form a flush surface across said plunger and the fluid flowpath through the connector is closed by said elastomeric plunger, and a second position wherein the slit portion is open and the elastomeric plunger is disposed over said blunt cannula such that said blunt cannula is in fluid communication with said connector port portion, said elastomeric plunger being pierced by said blunt cannula through said slit portion; and a biasing means for biasing said elastomeric plunger to said first position; whereby said connection port is sealed when said elastomeric plunger is in said first position within said connection port and the fluid flowpath through the connector is closed, and insertion of a compatible connector moves said elastomeric plunger over said blunt cannula to said second position, against the resistance of said biasing means, the insertion of a compatible connector being operative to open a fluid pathway from the inserted connector to said fluid conduit portion of said housing.

9. The self-sealing connector of claim 8, wherein said biasing means comprises compressed gas disposed within the interior chamber portion of said housing.

10. The self-sealing connector of claim 8, wherein said elastomeric plunger further comprises a collapsible elastomeric sleeve portion, integral with said elastomeric plunger and carried by said housing, and wherein said sleeve portion comprises said elastomeric biasing member.

11. The self-sealing connector of claim 9, wherein sir within said housing is pressurized by movement of said elastomeric plunger into said housing.

12. The self-sealing connector of claim 8, wherein said connector port portion comprises a female luer adapter.

13. The self-sealing connector of claim 8, further comprising a connector port member embodying said connector port portion, carried by said housing and forming a proximal end thereof, said connector port member retaining said elastomeric plunger in said self-sealing connector.

14. The self-sealing connector of claim 8, wherein said blunt cannula is unitary with said housing.

15. The self-sealing connector of claim 8, wherein said first end of said blunt cannula extends into said connection port portion, and said elastomeric plunger in said first position receives said first end of said blunt cannula in sealing movable engagement.

16. The self-sealing connector of claim 8, wherein said elastomeric plunger further comprises a proximal seal portion that is oversized in relation to said connector port portion, to sealingly fit movably within said connector port portion.

17. The self-sealing connector of claim 8, further comprising a lubricant applied to the elastomeric plunger whereby movement of said elastomeric plunger within said housing is facilitated.

18. The self-sealing connector of claim 17, wherein said plunger is formed of a self-lubricating elastomeric material.

19. A self-sealing connector adapted for making needleless sterile connections in the preparation, handling and administration of parental fluids, having a normally closed fluid flowpath therethrough which is opened by insertion of a compatible connector and closed by withdrawal of said compatible connector, comprising:

a housing having a first end and a second end, said housing defining an interior chamber therein, said first end of said housing defining a connector port portion having a substantially cylindrical interior portion, and said second end of said housing having a fluid conduit portion defining a fluid conduit therethrough, a blunt cannula, disposed within said interior chamber, having a first end adjacent said first end of said housing and a fluid flowpath therethrough which extends from said first end of said blunt cannula to said second end of said housing, the interior of said blunt cannula being in fluid communication with said fluid conduit at said second end of said housing portion, an elastomeric plunger, carried by said blunt cannula and housing, and adapted to movably and sealingly fit within the substantially cylindrical interior portion of the connector port opening at the first end of said housing, said plunger having a first position within said substantially cylindrical interior portion of said connector port opening, and said elastomeric plunger having a pre-slit portion therethrough which is closed in said first position, said elastomeric plunger having a second position within said interior portion of said connector port, wherein the normally closed slit portion is open, and said blunt cannula extends through said elastomeric plunger;

a collapsible sleeve portion of said elastomeric plunger, carried by said housing, said collapsible sleeve portion being elastically deformed when the piston portion is in said second position;

means for retaining a compressed gas in said chamber; whereby, said connection port is sealed when said plunger is in said first position within said connection port, and insertion of a compatible connector in said substantially cylindrical connection port portion moves said plunger to said second position, against the resistance of at least one of two biasing forces comprising a resorting force resulting from elastic deformation of the collapsible sleeve portion of said elastomeric plunger and further comprising a restoring force resulting from compression of gas within said interior chamber of said housing, the insertion of a compatible connector thereby opening a fluid pathway from the inserted compatible connector at said first end of said housing, to said second end of said housing, a biasing force returning the plunger to its first position upon withdrawal of said inserted compatible connector.

20. The self-sealing connector of claim 19, wherein said substantially cylindrical connector port opening comprises a female luer adapter.

21. The self-sealing connector of claim 19, further comprising a separate inlet connector member, embodying said connector port, carried by said housing and comprising a proximal end thereof, which inlet connector member embodies an annular ridge which acts to retain said plunger in said housing.

22. The self-sealing connector of claim 19, further comprising a lubricant applied to the elastomeric plunger whereby movement of said elastomeric plunger within said housing is facilitated.

23. The self-sealing connector of claim 19, wherein the blunt cannula is formed unitary with said housing.

24. The self-sealing connector of claim 19, wherein said housing component comprises a Y-site.

* * * * *

UNITED STATES PATENT AND TRADEMARK OFFICE
CERTIFICATE OF CORRECTION

PATENT NO. : 5,549,577
DATED : Aug. 27, 1996
INVENTOR(S) : Geoffrey S. Siegel, Karl R. Leinsing It is certified that error appears in the above-identified patent and that said Letters Patent is hereby corrected as shown below:

Column 8, claim 1, line 48, change "carded", to read --carried--

Column 8, claim 1, line 58, after "plunger", add --is--.

Column 11, claim 19, line 15, change "resorting", to read --restoring--.

Signed and Sealed this

Twenty-ninth Day of December, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,549,577
DATED        : August 27, 1996
INVENTOR(S)  : Geoffrey S. Siegel and Karl R. Leinsing It is certified that error appears in the above-identified patent and that said Letters Patent is hereby corrected as shown below:

Column 1,
Line 21, delete "Anterior" and insert -- interior --.

Column 2,
Line 26, delete "Needlelees" and insert -- Needleless --.

Column 3,
Line 5, delete "pro-slit" and insert -- pre-slit --.
Line 65, after "view of" and insert -- a --.

Column 4,
Line 32, delete "poet" and insert -- port --

Column 5,
Line 7, delete "Joined" and insert -- joined --.
Line 23, delete "whale" and insert -- while --.

Column 6,
Line 15, delete "to, a" and insert -- to a --.
Line 16, delete "byway" and insert -- by way --.
Line 59, delete "dietally" and insert -- distally --.

Column 7,
Line 6, delete "proximalend" and insert -- proximal end --.
Line 36, delete "lake" and insert -- like --.
Line 59, after "connector" insert -- is --.

Column 8,
Line 7, delete "fluid wall" and insert -- fluid will --.
Line 48, delete "carded" and insert -- carried --.
Line 58, after "plunger" insert -- is --.

Column 9,
Line 36, delete "carded" and insert -- carried --.
Line 45, delete "carded" and insert -- carried --.

UNITED STATES PATENT AND TRADEMARK OFFICE
CERTIFICATE OF CORRECTION

PATENT NO. : 5,549,577
DATED : August 27, 1996
INVENTOR(S) : Geoffrey S. Siegel and Karl R. Leinsing It is certified that error appears in the above-identified patent and that said Letters Patent is hereby corrected as shown below:

Column 10,
Line 11, delete "sir" and insert -- air --.

Column 11,
Line 15, delete "resorting" and insert -- restoring --.

Signed and Sealed this

Fourteenth Day of September, 2004

JON W. DUDAS
*Director of the United States Patent and Trademark Office*